US00PP36789P2

(12) United States Plant Patent
Whiting

(10) Patent No.: US PP36,789 P2
(45) Date of Patent: Jul. 1, 2025

(54) ***LAGERSTROEMIA* PLANT NAMED 'GV16103'**

(50) Latin Name: ***Lagerstroemia* hybrid**
Varietal Denomination: GV16103

(71) Applicant: James Dow Whiting, Clever, MO (US)

(72) Inventor: James Dow Whiting, Clever, MO (US)

(73) Assignee: GREENLEAF NURSERY CO., Park Hill, OK (US)

( * ) Notice: Subject to any disclaimer, the term of this patent is extended or adjusted under 35 U.S.C. 154(b) by 0 days.

(21) Appl. No.: 18/957,669

(22) Filed: Nov. 23, 2024

(51) Int. Cl.
*A01H 6/00* (2018.01)
*A01H 5/02* (2018.01)

(52) U.S. Cl.
USPC ..... Plt./252

(58) Field of Classification Search
USPC ..... Plt./252
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Lagerstroemia* plant named 'GV16103' that is characterized by its compact plant habit, its good disease resistance to leaf spot and powdery mildew, its flowers that are purple in color, and its floriferous blooming habit.

3 Drawing Sheets

Botanical classification: *Lagerstroemia* hybrid.
Variety denomination: 'GV16103'.

BACKGROUND OF THE INVENTION

The present invention relates to a new and distinct cultivar of *Lagerstroemia* of hybrid origin. The new *Lagerstroemia* will hereafter be referred to by its cultivar name, 'GV16103'. 'GV16103' is a new cultivar of crape myrtle grown for use as an ornamental landscape plant.

The new cultivar was derived from a controlled breeding program conducted by the Inventor in Clever, Missouri. The objective of the breeding program is to develop new cultivars of crape myrtle with compact plant habits, disease resistance, and improved winter hardiness.

'GV16103' originated as a seedling that arose from seed planted from open pollination of an unnamed and unpatented plant of *Lagerstroemia* from the Inventor's breeding program; reference no. GV1589, in summer of 2015. The male parent is therefore unknown. 'GV16103' was selected as a single unique plant in summer of 2022 from the resulting seedlings.

Asexual propagation of the new cultivar was first accomplished by softwood stem cuttings by the Inventor in Clever, Missouri in June of 2022. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GV16103' as a unique cultivar of *Lagerstroemia*.

1. 'GV16103' exhibits a compact plant habit.
2. 'GV16103' exhibits good disease resistance to leaf spot and powdery mildew.
3. 'GV16103' exhibits flowers that are purple in color.

4. 'GV16103' exhibits a floriferous blooming habit.

The parent of 'GV16103' differs from 'GV16103' in having a less compact plant habit, a less floriferous blooming habit, flowers that are pink in color, and has lower resistance to leaf spot. 'GV16103' can also be compared to the *Lagerstroemia* cultivars 'Orchid Cascade' (U.S. Plant Pat. No. 18,646) and 'Pocomoke' (not patented). 'Orchid Cascade' is similar to 'GV16103' in having a semi-weeping plant habit. 'Orchid Cascade' differs from 'GV16103' in having a less compact plant habit, less resistance to leaf spot and powdery mildew, and flowers that are lighter purple in color. 'Pocomoke' is similar to 'GV16103' in having a compact plant habit and good disease resistance. 'Pocomoke' differs from 'GV16103' in having a mounded plant shape and flowers that are pink in color.

BRIEF DESCRIPTION OF THE DRAWINGS

The accompanying color photographs illustrate the overall appearance and distinct characteristics of the new *Lagerstroemia*. The photographs were taken of a 3-year-old plant of the new cultivar as grown in a greenhouse in a 2-gallon container in Clever, Missouri.

The photograph on FIG. 1 provides a side view of 'GV16103' in bloom.

Figure 1:
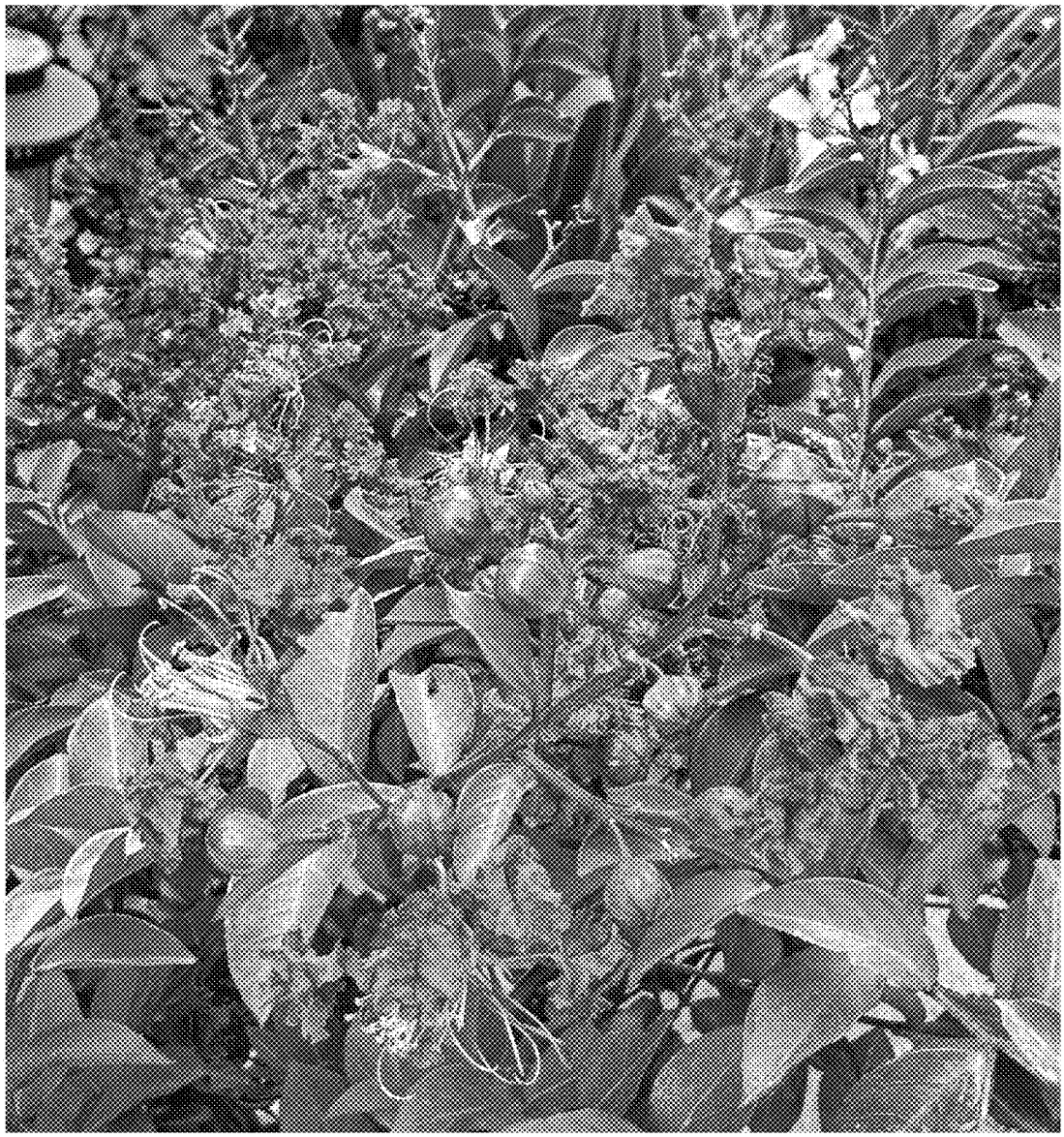
Figure 2:
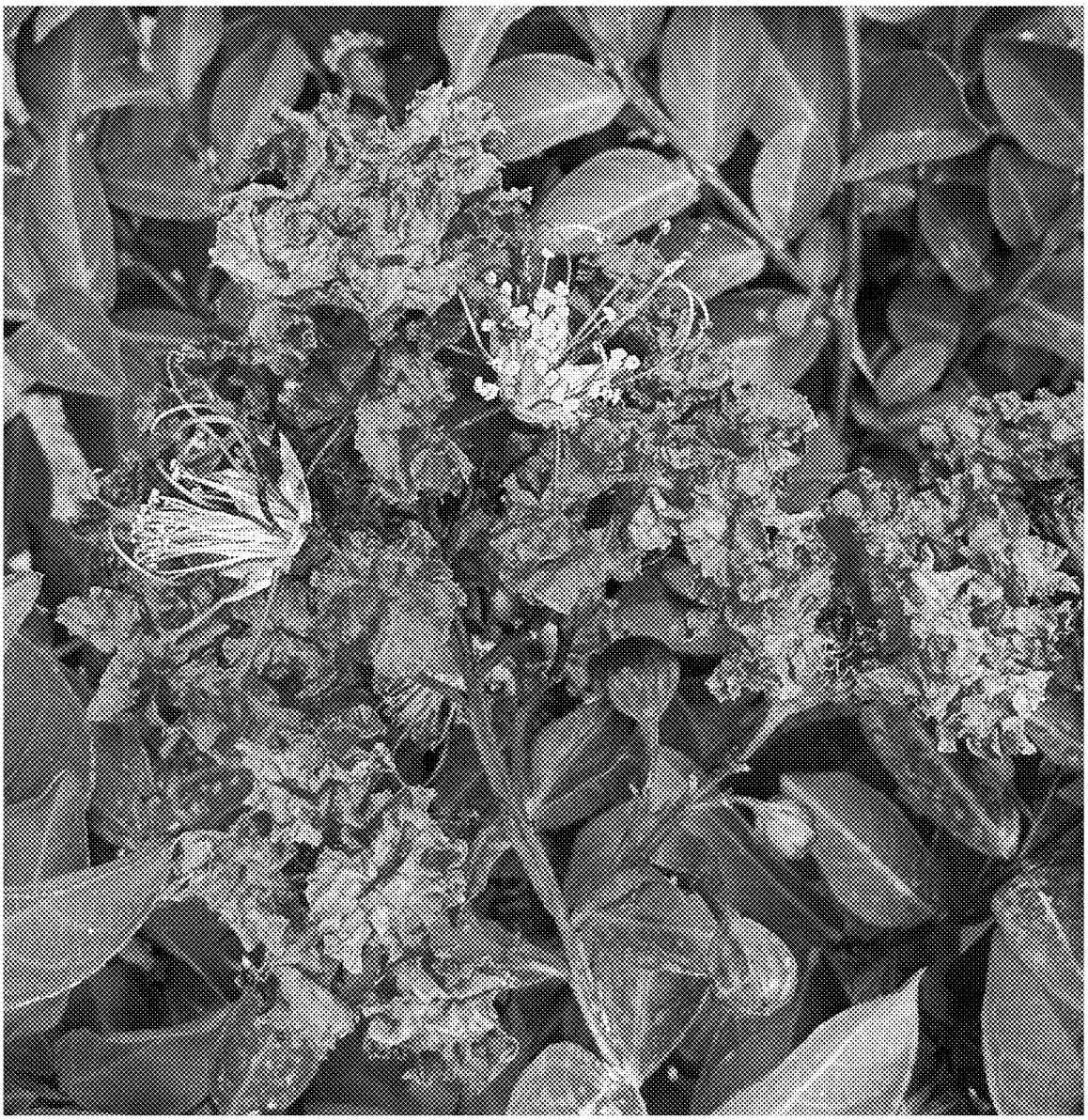

The photograph in FIG. 2 provides a close-up view of an inflorescence of 'GV16103'.

Figure 3:
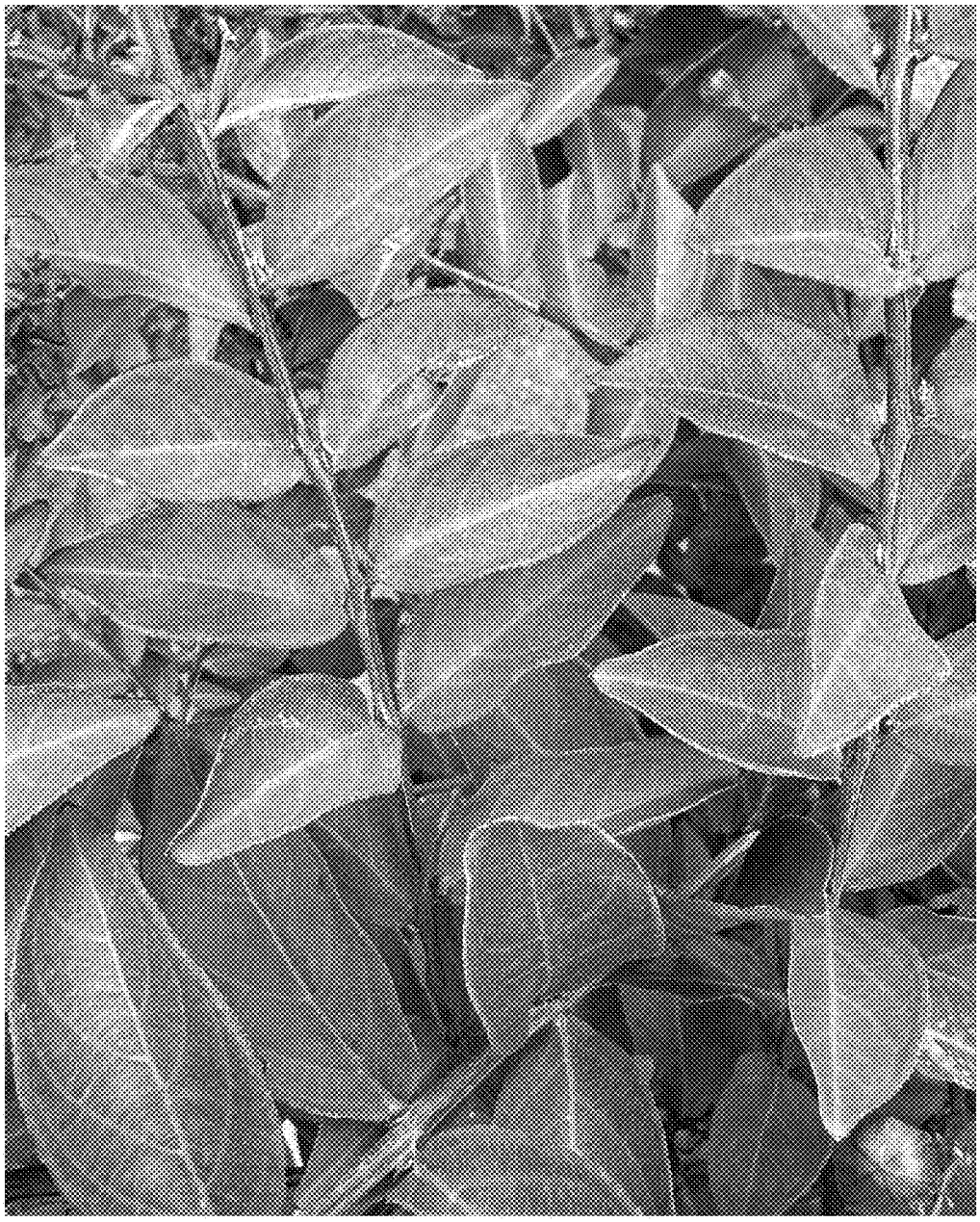

The photograph in FIG. 3 provides a close-up view of the foliage of 'GV16103'.

The colors in the photographs are as close as possible with the photographic and printing technology utilized and the color values cited in the Detailed Botanical Description accurately describe the colors of the new *Lagerstroemia*.

DETAILED BOTANICAL DESCRIPTION

The following is a detailed description of a 3-year-old plants of the new cultivar as grown in a greenhouse followed by outdoors in 2-gallon containers in full sun in Clever, Missouri. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—60 to 90 days, mid-summer into fall in Missouri.

*Plant type*.—Deciduous flowering shrub.

*Plant habit*.—Compact, semi-weeping.

*Height and spread*.—An average of 69 cm in height and 90 cm in width as grown in a container, as a mature plant in the landscape; average of 76 m in height and 1.1 m in width.

*Hardiness*.—At least in U.S.D.A. Zones 6 to 9.

*Diseases and pests*.—Good resistance to powdery mildew (caused by *Erysiphe lagerstroemiae*) and leaf spot (caused by *Cercospora lythracearum*) has been observed.

*Root description.*—199A in color, young roots are fibrous and fine.

*Root development.*—2 to 3 weeks for root initiation and one growing season to produce a young rooted plant.

*Propagation*.—Softwood or Semi-hardwood stem cuttings.

*Growth rate*.—Moderately vigorous.

Branch description:

*Branch shape*.—Quadrangular on young stems, oval on mature stems, round trunk.

*Branch color*.—Young; 187A in color, mature; 177B, old bark; 202C.

*Branch arrangement*.—Opposite.

*Branch size*.—Main; 10 cm in length, 1 cm in diameter, lateral; 48 cm in length, 2 mm in diameter, trunk; multi-branched, 2 to 3 cm in diameter at soil level.

*Branch surface*.—Young; glabrous and very glossy, mature; glossy, smooth, bark-like, truck, exfoliating, matte.

*Branch strength*.—Young; flexible and strong, mature; strong.

*Branching*.—Freely branching habit (without pruning), main branches; 10, lateral branches per main branch; 18.

*Branch aspect*.—Held in different angles from main, whorled.

*Internode length*.—An average of 2 cm.

Foliage description:

*Leaf shape*.—Elliptic.

*Leaf division*.—Single.

*Leaf base*.—Cuneate.

*Leaf apex*.—Acute.

*Leaf venation*.—Pinnate, upper surface; inconspicuous, lower surface 158A.

*Leaf margins*.—Entire.

*Leaf arrangement*.—Sub-opposite to alternate.

*Leaf attachment*.—Sessile.

*Leaf surface*.—Both surfaces glabrous and matte.

*Leaf size*.—An average of 3 cm in length and 1.5 cm in width.

*Leaf quantity*.—An average of 20 per lateral branch.

*Leaf color*.—Young and mature; upper and lower surface 138A, fall foliage; upper surface a blend of 178A and 185A, lower surface a blend of N187A and N187B.

Flower description:

*Inflorescence type*.—Terminal panicle.

*Lastingness of inflorescence*.—Inflorescences last for 4 to 6 weeks, individual flowers last an average of 1 day, self cleaning.

*Inflorescence size*.—An average of 17 cm in height and 10 cm in width.

*Inflorescence number*.—One per lateral branch.

*Flower number*.—An average of 25 flowers and flower buds per inflorescence.

*Flower fragrance*.—Faint fresh scent.

*Flower buds*.—Globose in shape, an average of 7 mm in length, 5 mm in depth, surface is glabrous and very glossy with six distinct lines at petal margins, color; a blend of 182A and 149C.

*Flower aspect*.—Upright to outward.

*Flower type*.—Rotate.

*Flower size*.—An average of 2 cm in height and 4 cm in diameter.

*Petals*.—Typically 5 to 6, rotate in arrangement, fan-shaped, curling downward, heavily ruffled, sagittate base with a long thin attachment 1 cm in length, 0.8 mm in diameter, rounded and ruffled apexes, both surfaces glabrous, satiny, an average of 1 cm in length and 1.5 in width, color; when opening and fully open upper and lower surface a blend of N81A and N81B.

*Calyx*.—Consists of 6 fused sepals, acute apices, an average of 4 mm in length and 3 mm in diameter, slightly rugose, glossy, glabrous on both surfaces, outer surface very glossy, color: young; outer surface 182A, inner surface 192A, mature; outer surface 145B, flushed at the tops with 182B, inner surface 192A.

*Peduncles*.—Strong, quadrangular, edges of angles slightly wavy, an average of 3 cm in length and 3 mm in diameter, surface is glabrous and glossy, 187A in color.

*Pedicels*.—Strong, quadrangular, edges of angles slightly wavy, an average of 8 mm in length and 1 mm in diameter, 187A in color, surface is very glossy and slightly covered in very short minute hairs 0.2 in length, NN155D in color.

Reproductive organs:

*Stamens.*—36 shorter curled stamens, clustered more in the center, 1.5 cm in length surrounded by 5 longer stamens, 2 cm in length, glabrous surface, anthers; on shorter stamens 13A in color, on longer stamens 143A and 202A in color, filaments; on shorter stamens 69A in color, on longer stamens 182A in color, pollen; abundant in quantity on shorter stamens, 14A in color.

*Pistils.*—1, an average of 1.5 cm in length, style; an average of 1.47 cm in length, color; 182A, stigma; rounded and flat in shape, 143A in color, 0.5 mm in diameter, ovary; superior, round, surface is glossy, 20B in color and 2 mm in diameter.

*Fruit and seed*.—Fruit; circular in shape, 8 mm in length and diameter, immature 144C in color, mature base 144C, top 144A, surface is glossy and glabrous, flesh is 144A and 145C in color, seed; each capsule contains about 20 seeds an average of 1.5 mm in length width, deltoid in shape, and 144C in color.

It is claimed:

1. A new and distinct cultivar of *Lagerstroemia* plant named 'GV16103' as herein illustrated and described.

* * * * *